United States Patent
Birklbauer et al.

(10) Patent No.: US 11,029,178 B2
(45) Date of Patent: Jun. 8, 2021

(54) DEVICE AND METHOD FOR OPERATING A HEATABLE SENSOR IN AN EXPLOSIVE ATMOSPHERE

(71) Applicant: E+E Elektronik Ges.m.b.H., Engerwitzdorf (AT)

(72) Inventors: Martin Birklbauer, Freistadt (AT); Karl Jahn, Gunskirchen (AT); Mario Schinnerl, Wartberg/Aist (AT)

(73) Assignee: E+E ELEKTRONIK GES.M.B.H., Engerwitzdorf (AT)

( * ) Notice: Subject to any disclaimer, the term of this patent is extended or adjusted under 35 U.S.C. 154(b) by 185 days.

(21) Appl. No.: 16/365,713

(22) Filed: Mar. 27, 2019

(65) Prior Publication Data

US 2019/0301901 A1 Oct. 3, 2019

(30) Foreign Application Priority Data

Mar. 28, 2018 (EP) .................................... 18164600

(51) Int. Cl.
*G01N 33/00* (2006.01)
*G01D 11/24* (2006.01)

(52) U.S. Cl.
CPC ......... *G01D 11/245* (2013.01); *G01N 33/004* (2013.01)

(58) Field of Classification Search
CPC .... G01D 11/245; G01D 21/00; G01N 33/004; G01N 33/0036; G01N 25/66
See application file for complete search history.

(56) References Cited

U.S. PATENT DOCUMENTS

| | | | |
|---|---|---|---|
| 5,121,627 A | 6/1992 | D'Aoust | |
| 5,984,126 A * | 11/1999 | Gordon | A62C 3/002 106/18.11 |
| 6,469,303 B1 | 10/2002 | Sun et al. | |
| 7,229,593 B1 * | 6/2007 | Ho | G01N 13/00 422/50 |
| 2005/0217889 A1 * | 10/2005 | Nelson | H01R 4/029 174/94 R |
| 2006/0162426 A1 | 7/2006 | Lange et al. | |

FOREIGN PATENT DOCUMENTS

| | | |
|---|---|---|
| DE | 8225525 U1 | 2/1983 |
| DE | 4026762 A1 | 5/1991 |
| EP | 1148317 B1 | 10/2001 |
| JP | 2007155639 A | 6/2007 |

\* cited by examiner

*Primary Examiner* — Suman K Nath
(74) *Attorney, Agent, or Firm* — Leydig, Voit & Mayer Ltd.

(57) ABSTRACT

An encapsulation device for operating a sensor in an explosive atmosphere includes a receiving space designed to receive the sensor and a protective housing having at least one gas-permeable wall portion that permits gas exchange between an interior space of the encapsulation device and an environment of the encapsulation device through the gas-permeable wall portion. A quenching volume is arranged to extend along an inner side of the protective housing and is filled with a filling material. The quenching volume at least partially surrounds the receiving space. A gas-permeable filter element is disposed between the quenching volume and the receiving space, and bounds the quenching volume with respect to the receiving space.

17 Claims, 4 Drawing Sheets

DEVICE AND METHOD FOR OPERATING A HEATABLE SENSOR IN AN EXPLOSIVE ATMOSPHERE

CROSS-REFERENCE TO PRIOR APPLICATION

Priority is claimed to European Patent Application No. EP 18164600.1, filed on Mar. 28, 2018, the entire disclosure of which is hereby incorporated by reference herein.

FIELD

The present invention relates to an encapsulation device for a sensor. It further relates to a sensor system and a method for operating a heatable sensor.

BACKGROUND

Many sensor types, including, inter alia, humidity sensors, dew-point sensors, CO2 sensors, and oxygen sensors, are energized with electrical power for operation thereof. As a result, the temperature at a surface of the sensor is typically higher than an ambient temperature. Such heat generation may be caused as a concomitant effect, for example by the operation of a lamp in the case of CO2 sensors, or be required for the sensor function itself, as in the case of some humidity sensors. Sensors during whose operation heat is generated are collectively referred to as "heatable sensors" herein.

The use of heatable sensors in explosion-prone areas, such as in an explosive atmosphere, may entail a risk of accidental ignition. In this connection, sources of danger include both the heated surface of the sensor and the potential for electrical sparking in a circuit of the sensor. Nevertheless, especially in explosion-prone areas, it is often desired to know parameters for whose measurement heatable sensors are required or advantageous.

Various techniques are known for reducing the ignition hazard during the operation of heatable sensors in explosion-prone areas. The currently applicable requirements for technical equipment with regard to explosion protection are defined, for example, in European technical standard EN60079-0 and the corresponding international standard IEC60079-0.

In the case of the ignition protection type "intrinsic safety," the electrical power input to the sensor or other electrical components is limited to such an extent that no electrical sparking hazard and no surface temperatures above a temperature limit can occur. The currently applicable requirements for intrinsic safety as the type of ignition protection are defined, for example, in European technical standard EN60079-11 and the corresponding international standard IEC60079-11. The protection type intrinsic safety generally imposes considerable limitations on the design and operation of sensors.

As an alternative, the ignition protection type "flameproof enclosure" requires the sensor or other electrical components to be enclosed in a mechanically rugged housing. The housing must be constructed to withstand a possible explosion occurring therein and to prevent explosive gases from escaping to the outside. The currently applicable requirements for a flameproof enclosure as the type of ignition protection are defined, for example, in European technical standard EN60079-1 and the corresponding international standard IEC60079-1. However, within the scope of the aforementioned standards, heatable sensors which are protected with this type of ignition protection alone are not permitted for use in an area in which an explosive atmosphere is present continuously, frequently, or for long periods of time ("zone 0").

As a further alternative, the ignition protection type "powder filling" requires the sensor or other electrical components to be filled with a material in the form of sand or glass beads. If, in this case, an ignition occurs at the sensor surface, the pressure rise is relatively low because of the small voids in the filling material. At the same time, the filling material cools the hot gases, so that when they exit, their temperature is no longer high enough to present an ignition hazard. The currently applicable requirements for a powder filling as the type of ignition protection are defined, for example, in European technical standard EN60079-5 and the corresponding international standard IEC60079-5. However, within the scope of the aforementioned standards, heatable sensors which are protected with this type of ignition protection alone are also not permitted for use in an area in which an explosive atmosphere is present continuously, frequently, or for long periods of time ("zone 0").

DE 82 25 525 U1 describes a probe element for measuring gas and gas/air mixtures. Unlike with a flameproof enclosure as the type of ignition protection, the probe is there embedded in a filling of sand or glass beads in accordance with a powder filling as an alternative type of ignition protection so as to promote entry of the gases to be measured into the probe housing. Depending on the particle diameter of the filling material used, this permits larger pores in the housing wall, thus facilitating the gas exchange with the environment of the probe.

With the aforementioned device, problems may arise due to the fact that the probe is embedded in the filling material. This precludes its use with some contact-sensitive probes. Moreover, this makes it more difficult or impossible to remove or insert probes from or into the housing, for example for replacement or servicing thereof. Further problems may arise due to the fact that, when used with a heatable sensor, its use in an explosive atmosphere still involves a significant hazard, for example when the power input to the sensor, respectively its heat output, exceeds corresponding limit values defined in the standard, for example for intrinsic safety as the type of ignition protection. In such a case, moreover, only one type of protection would be used, which also may not be in compliance with current redundancy requirements, for example with regard to a "double fault condition."

SUMMARY

In an embodiment, the present invention provides an encapsulation device for operating a sensor in an explosive atmosphere. The encapsulation device includes a receiving space designed to receive the sensor and a protective housing having at least one gas-permeable wall portion that permits gas exchange between an interior space of the encapsulation device and an environment of the encapsulation device through the gas-permeable wall portion. A quenching volume is arranged to extend along an inner side of the protective housing and is filled with a filling material. The quenching volume at least partially surrounds the receiving space. A gas-permeable filter element is disposed between the quenching volume and the receiving space, and bounds the quenching volume with respect to the receiving space.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
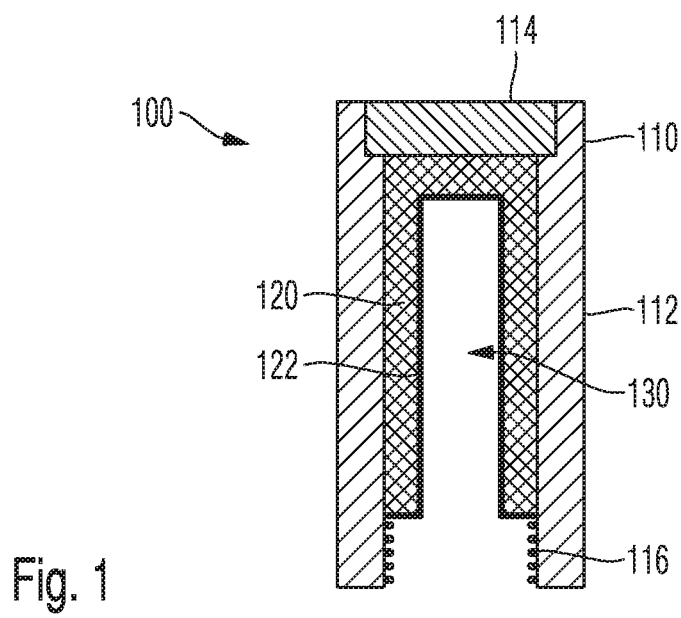
FIG. 1 shows an encapsulation device for a heatable sensor in accordance with an exemplary embodiment.

Embodiments of the present invention provide a technique that promotes the operation of a heatable sensor in particular in an explosive atmosphere.

One embodiment provides an encapsulation device for a sensor, in particular for operating the sensor in an explosive atmosphere, another embodiment provides a sensor system, and a further embodiment provides a method for operating a heatable sensor.

The encapsulation device includes a protective housing having at least one gas-permeable wall portion that permits gas exchange between an interior space of the encapsulation device and an environment of the encapsulation device through the gas-permeable wall portion, as well as a quenching volume arranged to extend along an inner side of the protective housing and filled with a filling material, the quenching volume at least partially surrounding a receiving space of the encapsulation device, which space is designed to receive a sensor. The encapsulation device further includes a gas-permeable filter element, which is disposed between the quenching volume and the receiving space and bounds the quenching volume with respect to the receiving space.

The filter element may be configured to prevent filling material from passing from the quenching volume into the receiving space. In particular, the filter element may be configured to prevent at least a portion of the filling material, for example any portion of the filling material, from passing from the quenching volume into the receiving space. Additionally or alternatively, the filter element may be configured to prevent mechanical contact between the filling material and/or the filter element and at least a portion of a sensor when the sensor is disposed in the receiving space.

The filter element may include stiff material, such as stiff plastic or metal. Additionally or alternatively, the filter element may include flexible material, such as a flexible plastic and/or metal fabric. In particular, the filter element may include a wire screen filter. Furthermore, a smallest particle size of the filling material may be larger than a largest pore size of the filter element. The filling material may include sand and/or glass beads.

The provision of the filter element facilitates handling the encapsulation device separately from a sensor. The filter element makes it possible, in particular, to prevent filling material from emerging from the quenching volume when no sensor is present in the receiving space of the encapsulation device. Moreover, the filter element makes it possible to prevent mechanical contact between a contact-sensitive sensing element of the sensor and the filling material and/or filter element.

The quenching volume may be configured to comply with the requirements for a powder filling as a first type of ignition protection with respect to the sensor. In this connection, the requirements for a powder filling as the type of ignition protection may be determined by technical standard EN60079-5 and/or technical standard IEC60079-5. The protective housing may be configured to comply with the requirements for a flameproof enclosure as a further type of ignition protection with respect to the sensor. In this connection, the requirements for a flameproof enclosure as the type of ignition protection may be determined by technical standard EN60079-1 and/or technical standard IEC60079-1.

The provision of the ignition protection types "powder filling" and "flameproof enclosure" may provide redundancy with respect to the present types of ignition protection. Such redundancy may allow the encapsulation device to be used in compliance with technical safety regulations even with heatable sensors which, according to the same technical safety regulations, are not permitted for use with only one of the ignition protection types.

The sensor may be a heatable sensor. The heatable sensor may include a humidity sensor, a dew-point sensor, a $CO_2$ sensor and/or an oxygen sensor. In particular, the heatable sensor may include a dew-point meter having a humidity sensor that has a bake-out function. The bake-out function may be provided for baking out chemical contaminants that could impair the functioning of the humidity sensor.

The gas-permeable wall portion may extend over at least a portion of a surface of the protective housing. In particular, the gas-permeable wall portion may extend over less than half of the surface, over more than half of the surface, or over the entire surface of the protective housing. The gas-permeable wall portion may include a sintered metal component. Additionally or alternatively, the gas-permeable wall portion may include stainless steel, in particular a sintered stainless steel component.

The encapsulation device may be configured for use in a measurement volume at any pressure, at least in the range of from 1 bar to 100 bar (see page 14), in particular in the range of from 0.5 bar to 300 bar, and specifically in the range of from 0 bar to 300 bar.

The encapsulation device may include at least one mounting element for mounting the encapsulation device at a pass-through opening. The pass-through opening may be provided in a wall of a measurement volume to allow the heatable sensor to be inserted into the measurement volume. The mounting element may include at least one thread. The measurement volume may include a vessel and/or a duct.

Alternatively, the encapsulation device may include at least one mounting element for freely mounting the encapsulation device within the measurement volume.

The encapsulation device may include a retractable fitting. The retractable fitting may allow insertion of the sensor into the receiving space of the encapsulation device and/or removal of the sensor from the receiving space of the encapsulation device through the pass-through opening. Furthermore, the retractable fitting may allow the pass-through opening to be reversibly closed when the sensor is removed. The mounting element of the encapsulation device may be provided on the retractable fitting.

Another embodiment of the present invention provides a sensor system. The sensor system includes a sensor and an encapsulation device of the type presented here, in which the receiving space of the encapsulation device is configured to receive the sensor.

The sensor of the sensor system may be disposed in the receiving space of the encapsulation device. In this connection, the sensor and the encapsulation device may be sealed together by a glass potting compound. The glass potting compound may have a thickness of 3 mm or more.

The sensor may be a heatable sensor. Furthermore, the encapsulation device may be configured to distribute and dissipate heat released from the heatable sensor. The distribution and dissipation of heat may be effected in such a way that, under the measurement conditions intended for the sensor system, a highest surface temperature at an outer side of the encapsulation device is lower than a highest surface temperature of the heatable sensor. The intended measurement conditions may include an ambient temperature of the sensor system within an intended temperature range and/or an ambient pressure of the sensor system within an intended pressure range.

The heatable sensor may have an electrical power greater than a power limit for intrinsic safety as the type of ignition protection with respect to the heatable sensor. In this connection, the highest surface temperature at the outer side of the encapsulation device may be lower than a temperature limit for explosion protection with respect to the heatable sensor. The temperature limit for explosion protection may be equal to a temperature limit for "intrinsic safety" as the type of ignition protection. Additionally or alternatively, the power limit and/or the temperature limit may be at least partially, in particular completely, determined by technical standards EN60079-11 and EN60079-0 and/or technical standards IEC60079-11 and IEC60079-0.

According to another embodiment, a method for operating a heatable sensor, in particular in an explosive atmosphere, is provided. The method includes providing, in a measurement volume, an encapsulation device for a heatable sensor, the encapsulation device including a protective housing having at least one gas-permeable wall portion that permits gas exchange between an interior space of the encapsulation device and an environment of the encapsulation device through the gas-permeable wall portion, as well as a quenching volume arranged to extend along an inner side of the protective housing and filled with a filling material, the quenching volume at least partially surrounding a receiving space of the encapsulation device, which space is designed to receive the heatable sensor, and further providing a heatable sensor disposed in the receiving space of the encapsulation device. The encapsulation device is configured to distribute and dissipate heat released from the heatable sensor in such a way that, under the intended operating conditions, a highest surface temperature at an outer side of the encapsulation device is lower than a highest surface temperature of the heatable sensor. The method further includes energizing the heatable sensor with electrical power, the electrical power being selected such that it is greater than a power limit for intrinsic safety as the type of ignition protection with respect to the heatable sensor, and that the highest surface temperature at the outer side of the encapsulation device is lower than a temperature limit for explosion protection with respect to the heatable sensor.

In this connection, the temperature limit for explosion protection may be equal to a temperature limit for intrinsic safety as the type of ignition protection.

FIG. 1 shows an encapsulation device 100 in schematic form. Encapsulation device 100 includes a protective housing 110 having a housing wall 112 with a gas-permeable wall portion 114 therein. Provided on an inner side of protective housing 110 is a quenching volume 120 filled with a filling material. Quenching volume 120 is bounded by a gas-permeable filter element 122 with respect to a receiving space 130 of encapsulation device 100. In the example shown, encapsulation device 100 further includes an enclosure thread 116 for reversibly mounting encapsulation device 100 to a sensor housing, for example.

Encapsulation device 100 is intended to allow a sensor, in particular a heatable sensor, to be operated in explosion-prone areas. To this end, receiving space 130 is configured to receive a sensor. In particular, protective housing 110 and quenching volume 120 are configured to enclose a surface of the sensor with respect to an environment of encapsulation device 100 in a way that reduces an ignition hazard presented by the sensor with respect to an explosive gas mixture in the environment of encapsulation device 100. In this connection, quenching volume 120 performs at least some of the above-described functions of a powder filling. For example, quenching volume 120 reduces a free volume inside encapsulation device 100, in which pressure may build up in the event of an explosion. At the same time, the filling material present in quenching volume 120 cools any ignited gases before they reach housing wall 112 and possibly escape to the outside through gas-permeable wall portion 114.

In the case of a conventional powder filling, the component to be encapsulated is typically embedded directly in filling material in a housing. In contrast, filter element 122 of encapsulation device 100 ensures that quenching volume 120 is bounded with respect to receiving space 130, and thus also with respect to a sensor possibly present therein. This allows encapsulation device 100, including quenching volume 120, to be provided and handled separately. In conjunction with suitably configured sensors or sensor housings, this allows a sensor to be easily provided with a quenching volume as an encapsulation as needed and according to the operating conditions, for example by screwing encapsulation device 100 with its enclosure thread 116 onto a thread of the sensor housing. At the same time, removal of encapsulation device 100 from the sensor housing allows easy access to the sensor, for example for replacement and maintenance purposes, without thereby adversely affecting or damaging the quenching volume.

Filter element 122 prevents filling material from passing from quenching volume 120 into receiving space 130. This makes it possible to prevent contact between portions of the filling material and at least certain regions of an inserted sensor. This allows encapsulation device 100 to be used even with sensors which are not suitable for being embedded directly in filling material in connection with a conventional powder filling. This is the case, for example, with some mechanically sensitive sensing elements, as well as with sensors which require for their operation a free sensor volume, which would be blocked by a conventional powder filling. In this connection, in some examples, filter element 122 is also configured such that it does not come into contact with mechanically sensitive portions of the sensor to be used.

In some examples, the filling material in quenching volume 120 includes sand and/or glass beads. A smallest particle size of the filling material and a largest pore size of filter element 122 are matched in such a way that no portions of the filling material will pass through pores of filter element 122. Furthermore, in some examples, filter element 122 is configured sufficiently rigid to ensure a predetermined position of filter element 122 relative to a sensor disposed in receiving space 130, for example a predetermined distance between a sensing element of the sensor and filter element 122. In this connection, filter element 122 may take the form of a wire screen filter, for example.

In further examples, filter element 122 is sufficiently flexible to allow quenching volume 120 to conform to at least portions of a surface of a sensor received in encapsulation device 100. This makes it possible to reduce a free volume at the surface of the sensor, in which pressure builds up in the event of an explosion. In this case, filter element 122 includes, for example, a flexible fabric, such as flexible plastic fabric.

In some examples, quenching volume 120 and filter element 122 are designed, in terms of materials and dimensions, in such a way that they comply with the technical requirements for a powder filling as the type of ignition protection with respect to the designated sensor. Examples of such requirements can be found in European standard EN60079-5 and the corresponding international standard IEC60079-5.

Protective housing 110 bounds quenching volume 120 with respect to an environment of encapsulation device 100. Protective housing 110 is composed, for example, of metal, in particular stainless steel, and/or another mechanically rugged material. Gas-permeable wall portion 114 of protective housing 110 permits gas exchange between an environment of encapsulation device 100 and a sensor disposed therein. Gas exchange occurs through quenching volume 120 and the filling material present therein, as well as through filter element 122. In some examples, gas-permeable wall portion 114 includes a sintered metal component, for example a gas-permeable sintered stainless steel component.

In addition to quenching volume 120, protective housing 110 also improves an ignition protection effect of encapsulation device 100. For example, protective housing 110 at least partially contains a possible ignition of explosive gases occurring within encapsulation device 100 with respect to an environment of encapsulation device 100. While, in such case, gas-permeable wall portion 114 permits gas exchange between an environment of encapsulation device 100 and the sensor surface, the pores or channels within gas-permeable wall portion 114 are, in some examples, dimensioned such that, in the event of an explosion within encapsulation device 100, escaping are sufficiently cooled to reduce or rule out a risk of ignition in the environment of encapsulation device 100 due to the escaping gases.

In the example shown, gas-permeable wall portion 114 extends along a top side of protective housing 110. In other examples, gas-permeable wall portion 114 includes additional and/or other parts of the surface of protective housing 110. For example, in some examples, gas-permeable wall portion 114 extends over substantially the entire surface area of protective housing 110, in particular at least over substantially the entire region of quenching volume 120.

In some examples, protective housing 110 is configured to comply with the technical requirements for a flameproof enclosure as the type of ignition protection in accordance with the technical standards that are applicable at the intended location of use. Examples of such standards include European standard EN60079-1 and the corresponding international standard IEC60079-1.

In this connection, in some examples, quenching volume 120 is at the same time configured to comply with the technical standards that are applicable for a powder filling as the type of ignition protection at the intended location of use with respect to the designated sensor, as described hereinbefore. Thus, in these examples of encapsulation device 100, at least two types of ignition protection are implemented in combination. This allows encapsulation device 100 to be used, for example, with heatable sensors under conditions in which redundancy of ignition protection types is advantageous and/or required, for example with regard to a "double fault condition." Thus, encapsulation device 100 makes it possible to extend the range of possible applications of certain sensors in explosion-prone areas, for examples in zones which have to meet increased safety requirements because explosive atmospheres are frequently present. Regulations regarding the combination of several types of ignition protection are defined, for example, in European technical standard EN60079-26 as well as the corresponding international standard IEC60079-26.

Figure 2:
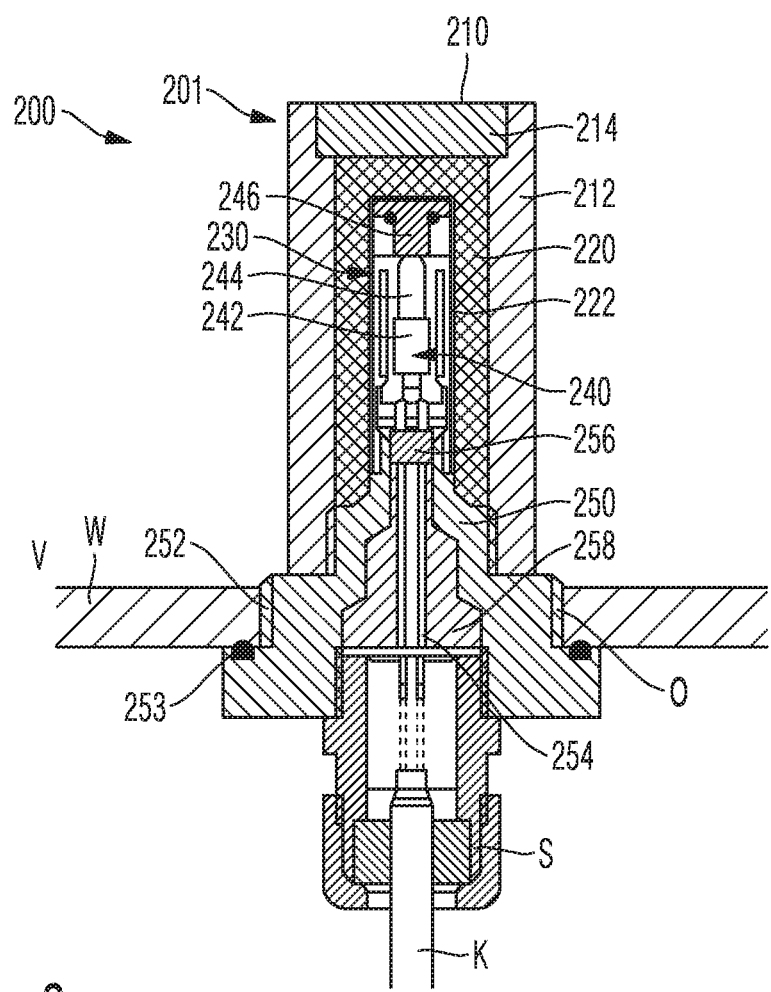
FIG. 2 shows a sensor system including an encapsulation device and a heatable sensor in accordance with an exemplary embodiment.

FIG. 2 schematically shows a sensor system 200 having an encapsulation device 201 and a sensor 240 disclosed therein. Encapsulation device 201 is, for example, an encapsulation device as described in connection with FIG. 1. Moreover, encapsulation device 201 is configured to receive sensor 240.

Encapsulation device 201 of sensor system 200 includes a protective housing 210 having a housing wall 212 with a gas-permeable wall portion 214 therein. Furthermore, a quenching volume 220 is arranged to extend along an inner side of protective housing 210, the quenching volume being bounded by a filter element 222 with respect to a receiving space 230 of encapsulation device 201. What has been said with respect to these features in connection with the encapsulation device 100 of FIG. 1 applies here correspondingly.

Sensor 240 is disposed in receiving space 230 of encapsulation device 201 and, in the example shown, includes a sensing element 242 adjacent to a sensor volume 244, which is bounded by a filter cap 246. Sensing element 242 is disposed on a housing body 250 and electrically connected to a cable K by metal pins 254 extending through housing body 250.

Protective housing 210 is attached to housing body 250 in a mechanically rugged fashion, for example by one or more threads. Furthermore, in the example shown, sensor system 200 is disposed for measurements in a measurement volume V. For this purpose, protective housing 210 is inserted through an pass-through opening O in a wall W of measurement volume V. Moreover, housing body 250 is attached to wall W of measurement volume V in a mechanically rugged fashion, for example by at least one mounting element 252, for example by one or more threads. In the example shown, sensor system 200 further includes a wall seal 253 designed to seal the transition between wall W and housing body 250.

In the example shown, sensor 240 and housing body 250 are irreversibly sealed together by means of a glass potting compound 256. Metal pins 254 are arranged to extend through glass potting compound 256 for electrically contacting sensor 240. In some examples, glass potting compound 256 is designed to comply with applicable technical requirements, such as requirements for a flameproof enclosure as the type of ignition protection. In particular, in some examples, glass potting compound 256 has a thickness of at least 3 mm.

In some examples, sensor system 200, in particular encapsulation device 201, is designed for use in measurement volumes V over large pressure ranges. In some examples, the pressure range includes any pressure between 1 bar and 100 bar, for example any pressure between 0.5 bar and 300 bar, in particular any pressure between 0 bar and 300 bar.

Furthermore, metal pins 254 are secured in housing body 250 by a potting compound 258. In some examples, potting compound 258 includes a material different from that of glass potting compound 256, for example, plastic and/or resin. In the example shown, a cable gland S is provided for strain relief of a connection between metal pins 254 and cable K.

In some examples, sensor 240 is one that is intrinsically safe in accordance with technical standards applicable at the intended location of use, which means that a power input to sensor 240 is limited to such an extent that no surface temperatures that could present a hazard of ignition and that no electric discharges that could present a hazard of ignition can occur at sensor 240. If quenching volume 220 is suitably designed with regard to a powder filling and/or if protective housing 210 is suitably designed with regard to a flameproof enclosure, then sensor system 200 permits additional combinations, and thus redundancies, of implemented types of ignition protection in these cases. Thus, it is possible, for example, to implement at least three types of ignition protection at the same time, namely intrinsic safety, powder filling and flameproof enclosure. Thus, sensor system 200 makes it possible to further extend the range of possible applications of various sensors 240 in areas of use where a corresponding combination of ignition protection types is advantageous and/or required by technical circumstances or regulations.

In some examples, protective housing 210 is designed to absorb heat released by a heatable sensor 240 during its operation, and to dissipate such heat into measurement volume V or into an environment of measurement volume V. Due to the distribution of heat over the surface of protective housing 210 and its dissipation therethrough into the environment, a highest surface temperature at an outer side of protective housing 210 is lower than a highest surface temperature of sensor 240. In this way, protective housing 210 allows heatable sensors 240 to be safely operated in explosion-prone areas even at surface temperatures of sensor 240 which would otherwise not permit safe and/or reliable operation of sensor 240. In particular, in some examples of sensor system 200, encapsulation device 201 is configured and a power input to heatable sensor 240 selected such that, under the intended measurement conditions in measurement volume V with regard to, for example, an ambient temperature and an ambient pressure in measurement volume V, the power input to heatable sensor 240 is greater than would be permitted by the requirements for intrinsic safety as the type of ignition protection with respect to sensor 240, whereas a highest surface temperature at an outer side of encapsulation device 201 is lower than a temperature limit for explosion protection. In this connection, heatable sensor 240 includes, for example, a dew-point meter having a humidity sensor that has a bake-out function. In the manner described above, sensor system 200 promotes the use of heatable sensors 240 under operating conditions under which their use would otherwise not be permitted by technical requirements and/or regulations.

Figure 3:
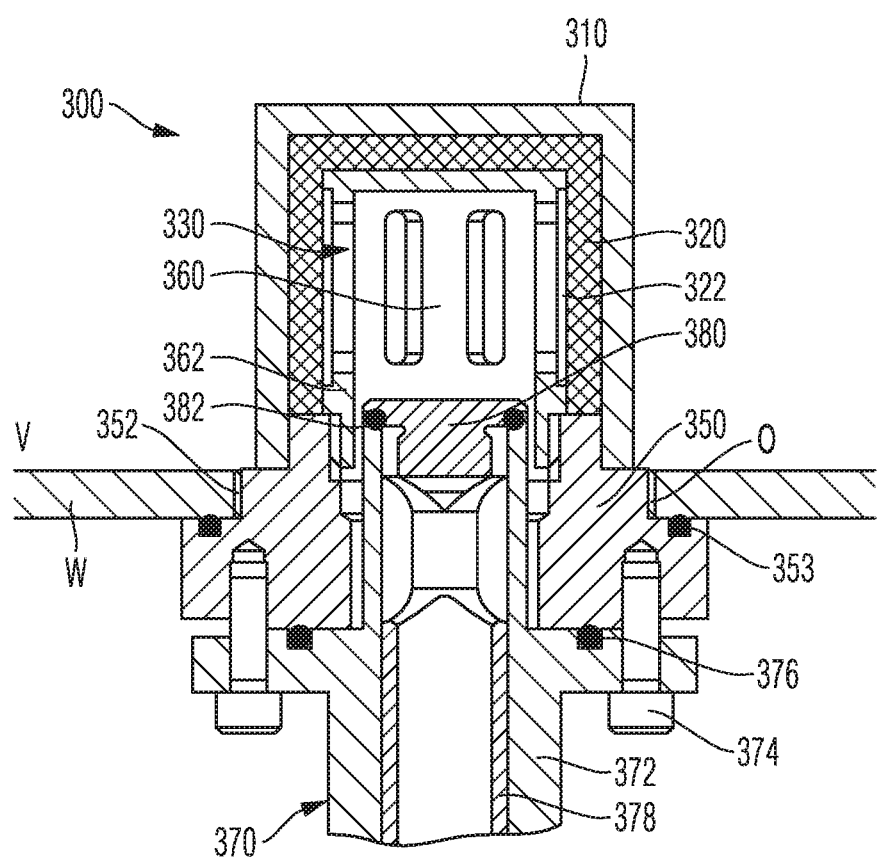
FIG. 3 depicts an encapsulation device for a heatable sensor in accordance with a further exemplary embodiment.

FIG. 3 shows a further encapsulation device 300 in schematic form. Similar to the aforementioned examples, encapsulation device 301 includes a protective housing 310 including at least one gas-permeable wall portion, as well as a quenching volume 320 arranged to extend along an inner side of protective housing 310 and bounded by a filter element 322 with respect to a receiving space 330 of encapsulation device 300. Furthermore, protective housing 310 is attached to a housing body 350. Housing body 350 is mounted in an pass-through opening O in the wall W of a measurement volume V by a mounting means 352 and sealed against wall W by a wall seal 353. What has been said with respect to these features in connection with the previous examples of FIGS. 1 and 2 applies here correspondingly, unless anything different is apparent from the following.

In a departure from sensor system 200 of FIG. 2, encapsulation device 300 is configured to allow a sensor to be installed and removed while encapsulation device 300 is in a mounted state. For this purpose, encapsulation device 300 includes a retractable fitting 370, which is attached at an outer side of housing body 350 by screws 374 and sealed by a fitting seal 376. Retractable fitting 370 has a push tube 378. Push tube 378 extends through fitting body 372 and housing body 350 to an installation volume 360 located inside receiving space 330 of encapsulation device 300. Push tube 378 is designed to allow a sensor to be introduced into or removed from installation volume 360 through push tube 378 from an outer side of the measurement volume while encapsulation device 300 is in a mounted state. The retractable fitting 370 shown is, for example, a retractable fitting of POSTBERG+Co. GmbH, as described in EP 1148317B1.

At the inner end of push tube 378, encapsulation device 300 has a push-tube end cover 380, which is sealed against fitting body 372 by a push-tube seal 382. When the sensor is removed, as illustrated in FIG. 3, push-tube end cover 380 allows receiving space 330 to be closed off pressure-tight from an environment of measurement volume V, whereas when inserting a sensor through push tube 378, push-tube end cover 380 is simultaneously moved to an open position.

Unlike the aforedescribed examples, encapsulation device 300 promotes the insertion, removal and/or replacement of a sensor from outside of measurement volume V. For example, encapsulation device 300 permits the sensor used to be easily serviced, replaced in case of a defect, or exchanged for another sensor, for example when the measurement requirements change.

Figure 4A:
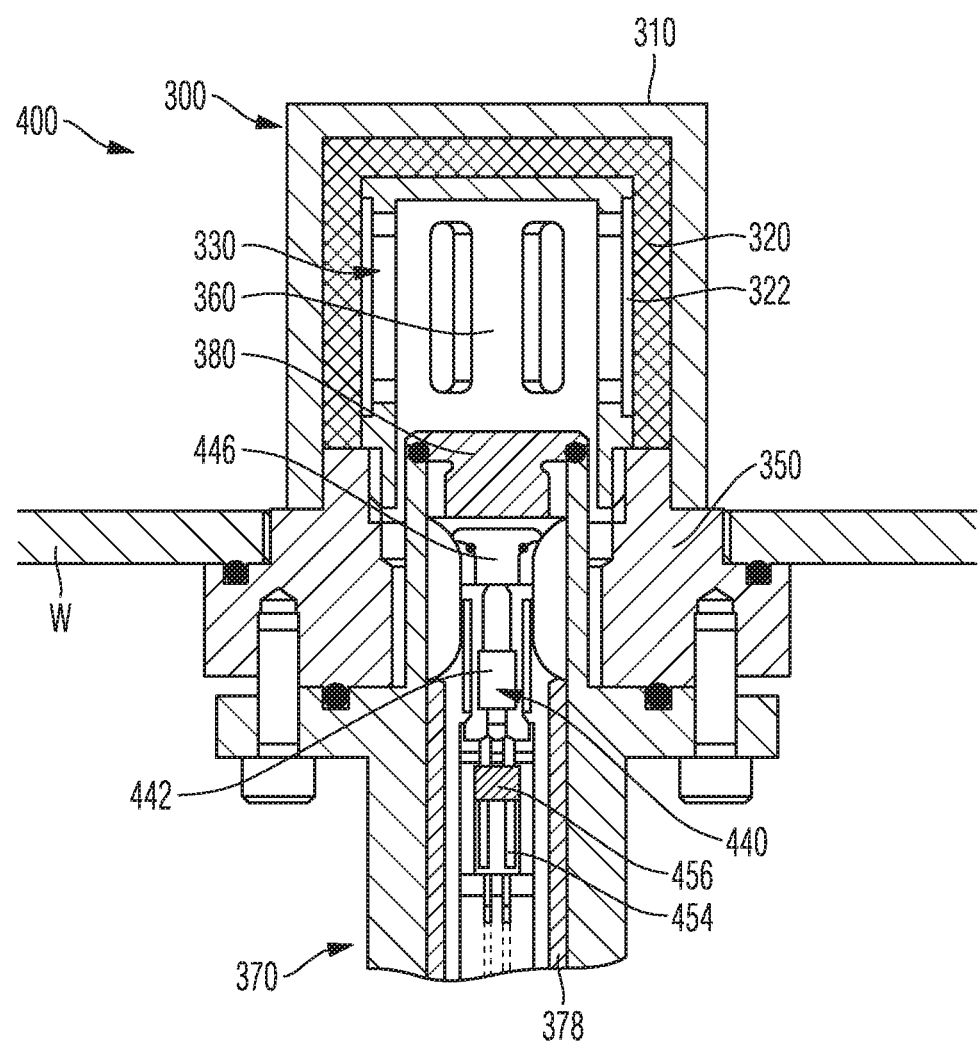
FIG. 4A shows a sensor system including an encapsulation device and a heatable sensor in accordance with another exemplary embodiment in a first position.

FIG. 4A shows another example of a sensor system 400. Sensor system 400 includes an encapsulation device 300 and a sensor 440. In the example shown, encapsulation device 300 is, for example, an encapsulation device as described in connection with FIG. 3. Like features are denoted by the same reference numerals as in FIG. 3.

Sensor 440 is disposed in push tube 378 of encapsulation device 300. Sensor 440 corresponds, for example, to the sensor 240, as described in connection with FIG. 2. In particular, sensor 440 also has a sensing element 442 as well as a filter cap 446 bounding a sensor volume. Also provided are metal pins 454 for electrically contacting sensing element 442, the metal pins being surrounded by a potting compound, for example a glass potting compound 456.

FIG. 4A shows sensor 440 in a position in which it is removed from receiving space 330 of sensor system 400. In this position, push-tube end cover 380 closes off receiving space 330 with respect to sensor 440. In the illustrated position, sensor system 400 is in a not-ready-for-measurement condition. Such a position occurs, for example, during insertion or removal of the sensor from measurement volume V.

Figure 4B:
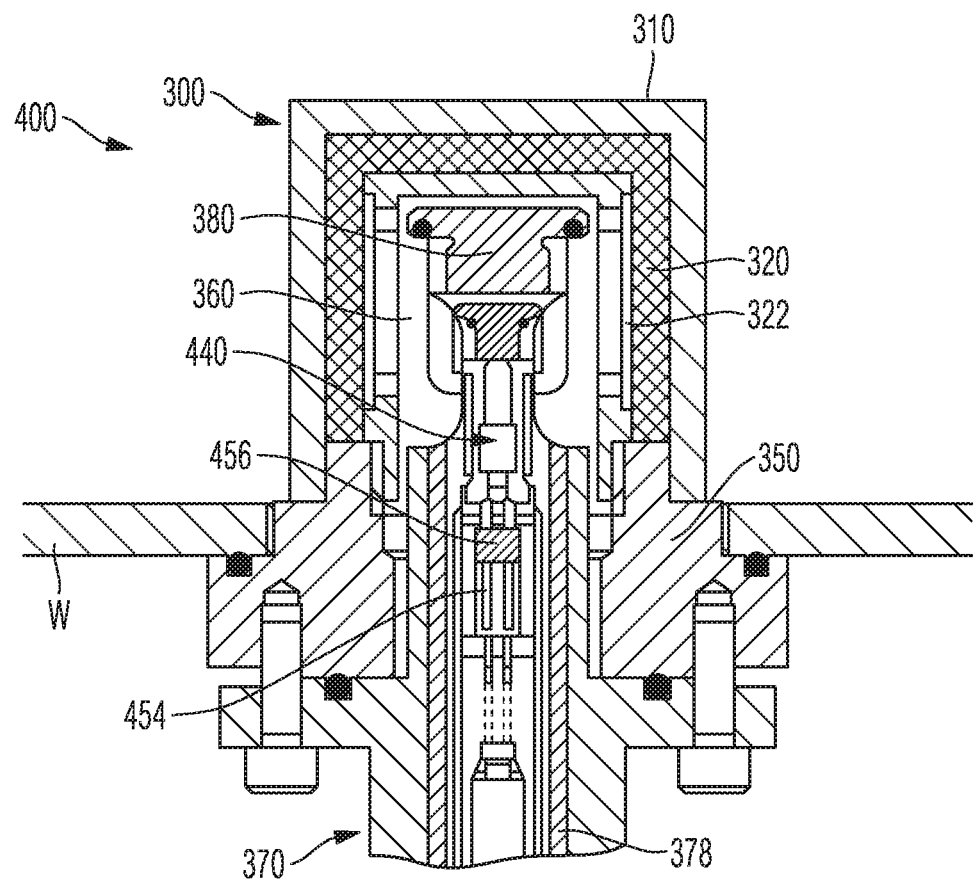
FIG. 4B shows the sensor system of FIG. 4A in a second position.

FIG. 4B shows another schematic view of sensor system 400. Unlike in FIG. 4A, sensor system 400 is here shown in a second position. In this position, sensor 440 has been pushed into receiving space 330 of encapsulation device 300 and push-tube end cover 380 has been pushed into an open position. In the illustrated position, sensor system 400 is in a ready-for-measurement condition. Thus, in the position shown, gas exchange is enabled between an environment of protective housing 310 and the sensor volume of sensor 440.

Some of the techniques presented hereinabove are described in the context of heatable sensors. It is understood, however, that the described techniques provide at least some of the advantages mentioned also in the context of non-heatable sensors and/or other functional components.

Figure 5:
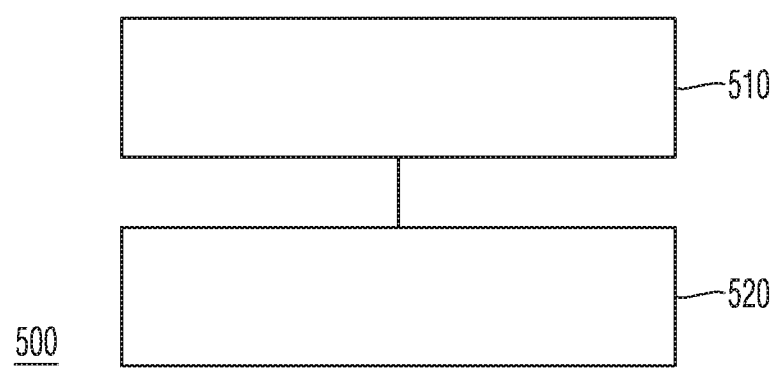
FIG. 5 shows a flow chart for a method for operating a heatable sensor.

FIG. 5 shows a flow chart for a method 500 for operating a heatable sensor, in particular in an explosive atmosphere. Method 500 includes providing an encapsulation device for a heatable sensor in a measurement volume as well as a heatable sensor in a receiving space of the encapsulation device, step 510. The encapsulation device includes a protective housing having a gas-permeable wall portion that permits gas exchange between a receiving space of the encapsulation device and an environment of the encapsulation device through the gas-permeable wall portion, as well as a quenching volume arranged to extend along an inner side of the protective housing and filled with a filling material, the quenching volume surrounding the receiving space that is designed to receive the heatable sensor. The encapsulation device is configured to distribute and dissipate heat released from the heatable sensor in such a way that, under the intended operating conditions, a highest surface temperature at an outer side of the encapsulation device is lower than a highest surface temperature of the heatable sensor.

Method 500 further includes energizing the heatable sensor with electrical power, step 520. The electrical power is selected such that it is greater than a power limit for intrinsic safety as the type of ignition protection with respect to the heatable sensor. At the same time, the electrical power is selected such that the highest surface temperature at the outer side of the encapsulation device is lower than a temperature limit for explosion protection with respect to the heatable sensor. A temperature difference between a surface of the sensor and the surface of the encapsulation device results, for example, from the distribution of heat over the surface of the encapsulation device and its dissipation therethrough.

The encapsulation device and the heatable sensor are, for example, of the types described hereinabove. As described in connection with FIG. 2, method 500 allows heatable sensors to be used even under operating conditions under which the use of such a sensor without providing a corresponding encapsulation device would not be sufficiently safe and/or reliable. This is made possible by the surface temperature of the encapsulation device being lower than the sensor temperature.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. An encapsulation device for operating a sensor in an explosive atmosphere, the encapsulation device comprising:
   a receiving space designed to receive the sensor;
   a protective housing having at least one gas-permeable wall portion that permits gas exchange between an interior space of the encapsulation device and an environment of the encapsulation device through the gas-permeable wall portion;
   a quenching volume arranged to extend along an inner side of the protective housing and filled with a filling material, the quenching volume at least partially surrounding the receiving space; and
   a gas-permeable filter element, which is disposed between the quenching volume and the receiving space and bounds the quenching volume with respect to the receiving space.

2. The encapsulation device as recited in claim 1, wherein the filter element is configured to prevent the filling material from passing from the quenching volume into the receiving space.

3. The encapsulation device as recited in claim 1, wherein the filter element is configured to prevent mechanical contact between the filling material and/or the filter element and at least a portion of a sensor when the sensor is disposed in the receiving space.

4. The encapsulation device as recited in claim 1, wherein the quenching volume is configured to comply with requirements for a powder filling as a first type of ignition protection with respect to the sensor, and wherein the protective housing is configured to comply with requirements for a flameproof enclosure as a further type of ignition protection with respect to the sensor.

5. The encapsulation device as recited in claim 1, wherein the gas-permeable wall portion includes a sintered metal component.

6. The encapsulation device as recited in claim 1, wherein the sensor is a heatable sensor.

7. The encapsulation device as recited in claim 1, wherein the filter element includes a wire screen filter.

8. The encapsulation device as recited in claim 1, wherein the encapsulation device is configured for use in a measurement volume at any pressure in the range of from 0 bar to 300 bar.

9. The encapsulation device as recited in claim 1, further comprising at least one mounting element configured to mount the encapsulation device at a pass-through opening provided in a wall of a measurement volume such that the sensor is insertable into the measurement volume.

10. The encapsulation device as recited in claim 9, further comprising a retractable fitting which allows insertion of the sensor into the receiving space and/or removal of the sensor from the receiving space through the pass-through opening and further allows the pass-through opening to be reversibly closed when the sensor is removed.

11. A sensor system comprising a sensor and the encapsulation device according to claim 1, wherein the receiving space of the encapsulation device is configured to receive the sensor.

12. The sensor system as recited in claim 11, wherein the sensor is disposed in the receiving space and sealed to the encapsulation device by a glass potting compound.

13. The sensor system as recited in claim 11, wherein the sensor is a heatable sensor, and wherein the encapsulation device is configured to distribute and dissipate heat released from the heatable sensor in such a way that, under measurement conditions intended for the sensor system, a highest surface temperature at an outer side of the encapsulation device is lower than a highest surface temperature of the heatable sensor.

14. The sensor system as recited in claim 13, wherein the heatable sensor has an electrical power greater than a power limit for intrinsic safety as the type of ignition protection with respect to the heatable sensor, and the highest surface temperature at the outer side of the encapsulation device is lower than a temperature limit for explosion protection with respect to the heatable sensor.

15. The encapsulation device as recited in claim 1, wherein the filling material includes sand and/or glass beads.

16. The encapsulation device as recited in claim 15, wherein the filter element is configured to prevent the filling material from passing from the quenching volume into the receiving space, and to prevent mechanical contact of the filling material with a sensor disposed in the receiving space.

17. A method for operating a heatable sensor in an explosive atmosphere, the method comprising:
providing, in a measurement volume, an encapsulation device for a heatable sensor, the encapsulation device comprising:
a receiving space designed to receive the heatable sensor,
a protective housing having at least one gas-permeable wall portion that permits gas exchange between an interior space of the encapsulation device and an environment of the encapsulation device through the gas-permeable wall portion,
a quenching volume arranged to extend along an inner side of the protective housing and filled with a filling material, the quenching volume at least partially surrounding the receiving space, the encapsulation device being configured to distribute and dissipate heat released from the heatable sensor in such a way that, under the intended operating conditions, a highest surface temperature at an outer side of the encapsulation device is lower than a highest surface temperature of the heatable sensor, and
a gas-permeable filter element, which is disposed between the quenching volume and the receiving space and bounds the quenching volume with respect to the receiving space;
providing the heatable sensor in the receiving space of the encapsulation device; and
energizing the heatable sensor with electrical power, the electrical power being selected such that it is greater than a power limit for intrinsic safety as the type of ignition protection with respect to the heatable sensor, and such that the highest surface temperature at the outer side of the encapsulation device is lower than a temperature limit for explosion protection with respect to the heatable sensor.

\* \* \* \* \*